United States Patent [19]

Cassidy et al.

[11] 4,168,202

[45] Sep. 18, 1979

[54] PROCESS FOR PRODUCING ANTIBIOTICS

[75] Inventors: Patrick J. Cassidy, Rahway; Robert T. Goegelman, Linden; Edward O. Stapley, Metuchen, all of N.J.; Sebastian Hernandez, Madrid, Spain

[73] Assignee: Merck & Co., Inc., Rahway, N.J.

[21] Appl. No.: 813,908

[22] Filed: Jul. 8, 1977

Related U.S. Application Data

[62] Division of Ser. No. 680,831, Apr. 28, 1976, abandoned.

[51] Int. Cl.$^2$ .................................................. C12D 9/14
[52] U.S. Cl. ................................... 435/121; 260/326.9
[58] Field of Search ........................................ 195/80 R

[56] References Cited

PUBLICATIONS

Chemical Abstracts, vol. 72, 11387u (1970).

*Primary Examiner*—Alvin E. Tanenholtz
*Attorney, Agent, or Firm*—Hesna J. Pfeiffer; James A. Arno; Julian S. Levitt

[57] ABSTRACT

The antibiotics MSD 890A$_2$ and MSD 890A$_5$ and pharmaceutically acceptable salts thereof (hereinafter referred to as antibiotics 890A$_2$ and 890A$_5$) are active against both gram-positive and gram-negative bacteria. The antibiotics are produced by growing species of Streptomyces on suitable fermentation media.

2 Claims, No Drawings

PROCESS FOR PRODUCING ANTIBIOTICS

This is a division of application Ser. No. 680,831, filed Apr. 28, 1976 and now abandoned.

BACKGROUND OF THE INVENTION

The discovery of the remarkable antibiotic properties of penicillin stimulated great interest in this field which has resulted in the finding of many other valuable antiobiotic substances such as: other penicillins, cephalosporins, streptomycin, bacitracin, tetracyclines, chloramphenicol, erythromycins and the like. In general the antibacterial activity of each of these antibiotics does not include certain clinically important pathogenic bacteria. For example, some are principally active against only gram-positive types of bacteria. Acquired resistance over the course of widespread use of existing antibiotics in the treatment of bacterial infection has caused a serious resistance problem to arise.

Accordingly, the deficiencies of the known antibiotics have stimulated further research to find other antibiotics which will be active against a wider range of pathogens as well as resistant strains of particular microorganisms.

This further research has lead to the discovery of the thienamycin family of antibiotics of which the compounds of the present invention are members. Other members of the thienamycin family of antibiotics are described in the applications Jean S. Kahan, Frederick M. Kahan, Edward O. Stapley, Robert T. Goegelman and Sebastian Hernandez, U.S. Pat. Ser. No. 632,938, filed Nov. 18, 1975 which is a divisional application of the co-pending application Jean S. Kahan, Frederick M. Kahan, Edward O. Stapley, Robert T. Goegelman and Sebastian Hernandez, U.S. Pat. Ser. No. 526,992, filed Nov. 25, 1974; Robert T. Goegelman and Frederick M. Kahan, U.S. Pat. Ser. No. 613,822, filed Sept. 18, 1975 which is a continuation-in-part of the co-pending application Robert T. Goegelman and Frederick M. Kahan, U.S. Pat. Ser. No. 534,382, filed Dec. 19, 1974, now abandoned; Patrick J. Cassidy, Robert T. Goegelman, Edward O. Stapley and Sebastian Hernandez, U.S. Pat. Ser. No. 634,300, filed Nov. 21, 1975; Jean S. Kahan, Frederick M. Kahan, Robert T. Goegelman, Edward O. Stapley and Sebastian Hernandez, U.S. Pat. Ser. No. 634,301, filed Nov. 21, 1975; and Jean S. Kahan and Frederick M. Kahan, U.S. Pat. Ser. No. 634,560, filed Nov. 24, 1975.

SUMMARY OF THE INVENTION

This invention is directed to new members of the thienamycin family of antibiotic agents. More particularly, it is concerned with new antibiotic substances, herein designated 890$A_2$ and 890$A_5$. The invention encompasses the antibiotics in dilute forms, as crude concentrates and in pure forms.

It is an object of the present invention to provide new and useful antibiotics which are highly effective in inhibiting the growth of various gram-negative and gram-positive microorganisms. Another object is to provide a process for the preparation of these novel antibiotic substances by the fermentation of nutrient media with species of Streptomyces. Other objects will be apparent from the detailed description of this invention hereinafter provided.

The novel antibiotic substances of the present invention are produced by growing under controlled conditions new strains of *Streptomyces flavogriseus*.

Based upon extensive taxonomic studies the strains of microorganisms used in the present invention were identified as belonging to the species *Streptomyces flavogriseus* and have been designated MA-4434 and MA-4600 in the culture collection of MERCK & CO., Inc., Rahway, N.J. A culture of each thereof has been placed on permanent deposit without restrictions as to availability with the culture collection of the Northern Regional Laboratories, Northern Utilization Research and Development Division, Agricultural Research Service, U.S. Department of Agriculture, Peoria, Ill., and are available to the public under accession No. NRRL 8139 and 8140, respectively.

*Streptomyces flavogriseus* NRRL 8139 and NRRL 8140 each produce both antibiotics 890$A_2$ and 890$A_5$ which are isolated in substantially pure form from the fermentation broth.

The morphological and cultural characteristics of *Streptomyces flavogriseus* NRRL 8139 are set forth in the following table.

Morphology—Sporophores are branching, straight to flexuous chains of spores, forming tufts. Chains are more than 10 spores in length. Spores are spherical to oval—$0.9\mu \times 1.2\mu$ (970$\times$).

Cultural Characteristics

Oatmeal agar
    Vegetative growth—Reverse-yellowish tan, parchment-like growth;
    Aerial mycelium—Light gray edged with medium gray
    Soluble pigment—None.

Czapek Dox agar (sucrose nitrate agar)
    Vegetative growth—Reverse-brown edged with dark brown;
    Aerial mycelium—Medium gray, velvety;
    Soluble pigment—Slight browning of medium.

Egg albumin agar
    Vegetative growth—Reverse-yellowish tan edged with brown;
    Aerial mycelium—Medium gray mixed with yellowish gray (2dc) and grayed yellow (2db);
    Soluble pigment—Light yellowish tan.

Glycerol asparagine agar
    Vegetative growth—Reverse-yellowish tan, flat, spreading;
    Aerial mycelium—Velvety, light gray with a strong yellowish tone to gray (2dc);
    Soluble pigment—None.

Inorganic salts-starch agar
    Vegetative growth—Reverse-brown;
    Aerial mycelium—Medium gray, velvety;
    Soluble pigment—Light yellowish-tan.

Yeast extract-dextrose+salts agar
    Vegetative growth—Reverse-brown edged with very dark brown;
    Aerial mycelium—Dark gray mixed with a light gray, velvety;
    Soluble pigment—None.

Yeast extract-malt extract agar
    Vegetative growth—Reverse-dark brown;
    Aerial mycelium—Dark gray, velvety;
    Soluble pigment—None.

Skim milk agar
    Vegetative growth—Tan;

Aerial mycelium—Sparse, grayish;
Soluble pigment—Slight browning of medium;
Hydrolysis of casein—Good.

Litmus milk
 Vegetative growth—Moderate growth ring, dark tan;
 Aerial mycelium—None;
 Color—Purple;
 Coagulation and/or peptonization—Complete peptonization; becoming alkaline, pH 8.2.

Skim milk
 Vegetative growth—Moderate growth ring, tan;
 Aerial mycelium—None;
 Soluble pigment—Tan;
 Coagulation and/or peptonization—Complete peptonization; becoming alkaline, pH 8.0.

Tyrosine agar
 Vegetative growth—Reverse-dark brown;
 Aerial mycelium—Dark gray;
 Soluble pigment—Slight browning of medium;
 Decomposition of tyrosine—None.

Peptone-iron-yeast extract agar
 Vegetative growth—Tan;
 Aerial mycelium—Sparse, grayish;
 Soluble pigment—None;
 Melanin—None;
 $H_2S$ production—None.

Nutrient agar
 Vegetative growth—Reverse-light grayish brown edged with darker gray-brown;
 Aerial mycelium—Light gray edged with dark gray;
 Soluble pigment—None.

Nutrient starch agar
 Vegetative growth—Tan edged with gray
 Aerial mycelium—Medium gray edged with dark gray;
 Soluble pigment—None;
 Hydrolysis of starch—Good Nutrient gelatin agar
 Vegetative growth—Colorless edged with dark gray;
 Aerial mycelium—Grayish-white;
 Soluble pigment—None;
 Liquefaction of gelatin—Good.

Potato plug
 Vegetative growth—Good growth, heavily wrinkled;
 Aerial mycelium—Gray to greenish-gray;
 Soluble pigment—Slight browning of medium.

Loeffler's Blood serum
 Vegetative growth—Cream-colored;
 Aerial mycelium—None;
 Soluble pigment—None;
 Liquefaction—None.

Gelatin stabs
 Vegetative growth—Cream-colored;
 Aerial mycelium—None;
 Soluble pigment—None;
 Liquefaction of gelatin—Good.

All of the readings reported above were taken after three weeks incubation at 28° C. unless noted otherwise. The pH of the media used in these studies was approximately neutral, namely, pH 6.8–7.2. The color designations used in the description are in accordance with the definitions of the *Color Harmony Manual*, 4th Edition (1958), Container Corporation of America, Chicago, Illinois.

*Streptomyces flavogriseus* NRRL 8139 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2). Table I shows the utilization of these carbohydrate sources by *Streptomyces flavogriseus* NRRL 8139, + indicating good growth, ± poor growth, and — no growth on the particular carbohydrate.

TABLE I

| Glucose | + | Maltose | + |
|---|---|---|---|
| Aribinose | + | Mannitol | + |
| Cellulose | − | Mannose | + |
| Fructose | + | Raffinose | − |
| Inositol | − | Rhamnose | + |
| Lactose | + | Sucrose | ± |
| Xylose | + | | |

The amount of growth with change in temperature and the oxygen requirement by the microorganism is as follows:

Temperature range (Yeast extract-dextrose+salts agar);
 28° C.—Good
 37° C.—Good vegetative growth; no aerial hyphae
 50° C.—No growth Oxygen requirement (Stab culture in yeast extract-dextrose+salts agar);
 Aerobic The morphological and cultural characteristics of *Streptomyces flavogriseus* NRRL 8140 are set forth in the following table.

Morphology—Sporophores are branching, straight to flexuous chains of spores, forming tufts. Chains are more than 10 spores in length. Spores are spherical to oval—$0.9\mu \times 1.2\mu$ (970×).

Cultural Characteristics

Oatmeal agar
 Vegetative growth—Reverse-yellowish tan edged with dark brown;
 Aerial mycelium—Light gray edged with medium gray;
 Soluble pigment—None.

Czapek Dox agar (sucrose nitrate agar)
 Vegetative growth—Reverse-brown edged with dark brown;
 Aerial mycelium—Medium gray, velvety;
 Soluble pigment—None.

Egg albumin agar
 Vegetative growth—Reverse-grayish tan with sections of strong yellow tan;
 Aerial mycelium—Sections of medium gray, grayish white and yellowish gray (2dc);
 Soluble pigment—Very light tan.

Glycerol asparagine agar
 Vegetative growth—Yellowish tan;
 Aerial mycelium—Sparse, grayish;
 Soluble pigment—None.

Inorganic salts-starch agar
 Vegetative growth—Reverse-grayish cream;
 Aerial mycelium—Medium gray, velvety;
 Soluble pigment—None.

Yeast extract-dextrose—salts agar
 Vegetative growth—Reverse-dark brown;

Aerial mycelium—Dark gray mixed with a light gray, velvety;
Soluble pigment—None.
Yeast extract-malt extract agar
Vegetative growth—Reverse-dark brown;
Aerial mycelium—Dark gray, velvety;
Soluble pigment—None.
Peptone-iron-yeast extract agar
Vegetative growth—Tan;
Aerial mycelium—None;
Soluble pigment—None;
Melanin—None;
$H_2S$ production—None.
Nutrient agar
Vegetative growth—Light tan;
Aerial mycelium—None.
Soluble pigment—None.
Nutrient starch agar
Vegetative growth—Cream-colored;
Aerial mycelium—None;
Soluble pigment—None;
Hydrolysis of starch—Good.
Nutrient gelatin agar
Vegetative growth—Cream-colored;
Aerial mycelium—None;
Soluble pigment—None;
Liquefaction of gelatin—Good.
Gelatin stabs
Vegetative growth—Tan;
Aerial mycelium—None;
Soluble pigment—None;
Liquefaction of gelatin—Complete.
Skim milk agar
Vegetative growth—Tan;
Aerial mycelium—None;
Soluble pigment—None;
Hydrolysis of casein—Good.
Litmus milk
Vegetative growth—Tan growth ring;
Aerial mycelium—None;
Color—Brownish purple;
Coagulation and/or peptonization—Complete peptonization, becoming alkaline, pH 8.0.
Skim milk
Vegetative growth—Tan, moderate growth ring;
Aerial mycelium—None;
Soluble pigment—Light brown;
Coagulation and/or peptonization—Complete peptonization, becoming alkaline pH 8.5.
Potato plug
Vegetative growth—Good, tan colored;
Aerial mycelium—Very sparse, whitish;
Soluble pigment—None.
Loeffler's Blood serum
Vegetative growth—Cream-colored;
Aerial mycelium—None;
Soluble pigment—None;
Liquefaction—None.
Tyrosine agar
Vegetative growth—Tan;
Aerial mycelium—None;
Soluble pigment—Slight browning of medium;
Decomposition of tyrosine—Very slight.

All of the readings reported above were taken after three weeks incubation at 28° C. unless noted otherwise. The pH of the media used in these studies was approximately neutral, namely pH 6.8–7.2. The color designations used in the description are in accordance with the definitions of the *Color Harmony Manual*, 4th Edition (1958), Container Corporation of America, Chicago, Illinois.

*Streptomyces flavogriseus* NRRL 8140 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2) Table II shows the utilization of these carbohydrate sources by *Streptomyces flavogriseus* NRRL 8140 + indicating good growth, ± poor growth, and — no growth on the particular carbohydrate.

TABLE II

| Glucose | + | Maltose | + |
|---|---|---|---|
| Arabinose | + | Mannitol | + |
| Cellulose | − | Mannose | + |
| Fructose | + | Raffinose | ± |
| Inositol | ± | Rhamnose | + |
| Lactose | + | Sucrose | ± |
| Xylose | + | | |

The amount of growth with change in temperature and the oxygen requirement by the microorganism is as follows:

Temperature range (Yeast extract-dextrose+salts agar);
 28° C.—Good
 37° C.—Moderate vegetative growth; no aerial hyphae
 50° C.—No growth
Oxygen requirement (Stab culture in yeast extract-dextrose+salts agar);
 Aerobic It is to be understood that for the production of new antibiotics of this invention, the present invention is not limited to the organism, *Streptomyces flavogriseus* or to organisms fully answering the above growth and microscopic characteristics which are given for illustrative purposes. In fact, it is desired and intended to include the use of mutants produced from the described organism by various means, such as X-radiation, ultraviolet radiation, nitrogen mustard, phage exposure and the like.

The novel antibiotics of the invention, $890A_2$ and $890A_5$, are produced during the aerobic fermentation, under controlled conditions, of suitable aqueous nutrient media inoculated with strains of the organism, *Streptomyces flavogriseus*. Aqueous media, such as those employed for the production of other antibiotics, are suitable for producing $890A_2$ and $890A_5$. Such media contain sources of carbon, nitrogen and inorganic salts assimilable by the microorganism.

In general, carbohydrates such as sugars, for example, dextrose, glucose, fructose, maltose, sucrose, xylose, mannitol and the like and starches such as dextrin or such as grains, for example, oats, rye, cornstarch, corn meal and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, magnesium, phosphate, sulfate, chloride, carbonate, and like ions. Also included are trace metals such as cobalt, manganese and iron.

It should be noted that the media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 23° C. to 28° C. The initial pH of the nutrient media suitable for growing strains of the *Streptomyces flavogriseus* culture and producing antibiotics 890A$_2$ and 890A$_5$ can vary from about 6.0 to 8.0.

Although the novel antibiotics 890A$_2$ and 890A$_5$ are produced by both surface and submerged cultures, it is preferred to carry out the fermentation in the submerged state.

A small scale fermentation of the antibiotic is conveniently carried out by inoculating a suitable nutrient medium with antibiotic-producing culture and, after transfer to a production medium, permitting the fermentation to proceed at a constant temperature of about 28° C. on a shaker for several days.

The fermentation is initiated in a sterilized flask of nutrient medium via one or more stages of seed development. The nutrient medium for the seed stage may be any suitable combination of carbon and nitrogen sources. The seed flask is shaken in a constant temperature chamber at about 28° C. for one day, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flask are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 1 to 6 days while agitating and/or aerating the nutrient medium and maintaining the temperature at about 24° to 28° C. This method of producing antibiotics 890A$_2$ and 890A$_5$ is particularly suited for the preparation of large quantities of the antibiotics.

PHYSICAL AND CHEMICAL PROPERTIES OF ANTIBIOTICS 890A$_2$ AND 890A$_5$

PROPERTIES OF ANTIBIOTIC 890A$_2$

Antibiotic 890A$_2$ is an acidic substance which moves toward the positive pole on electrophoresis at neutral pH.

The sodium salt of antibiotic 890A$_2$ is a white powder as lyophilized from aqueous solution, and is very soluble in water.

The ultraviolet absorbance spectrum has maxima at 308 and 228 nm, and a minimum at 262 nm. The E% at 308 nm of the sodium salt of antibiotic 890A$_2$ in water at neutral pH is estimated to be greater than 490. The ratio of absorbance values, $A_{308}/A_{260}$, is 1.91 and $A_{308}/A_{228}$ is 1.02 for the best samples obtained; evidence of small quantities of impurities remaining in these samples suggest that the ratio may be slightly higher for a sample of ultimate purity.

More than 80% of the absorption at 308 nm may be eliminated by reaction with hydroxylamine, and a similar decrease is observed upon reaction with cysteine. The absorbance at 260 nm after such reactions increases by about one-fourth the magnitude of the $A_{308}$ decrease. Under the conditions described in the section headed Bioassay III for determining the HAEA$_{308}$ values, the reaction kinetics appear to be first order with a half-life at room temperature between 0.5 and 1.5 minutes.

The following table lists the 100 MHz-NMR signals for 890A$_2$ sodium salt in D$_2$O relative to the internal standard, sodium 2,2-dimethyl-2-silapentane-5-sulfonate, hereinafter referred to as DSS; chemical shifts are given in ppm and coupling constants in Hz; the apparent multiplicites are indicated.

1.33 (d, J=6, C$\underline{H}_3$—CH); 2.07 (S, C$\underline{H}_3$C=O);
3.15 (m, C—C$\underline{H}_2$—C); 3.69 (m, >C$\underline{H}$—C=O);
~4.3 (>C$\underline{H}$N and >C$\underline{H}$—OH), 6.09 and 7.12 (doublets,
J=13.5, S—C$\underline{H}$=C$\underline{H}$—N).

The antibiotic potency of 890A$_2$, measured on *Vibrio percolans* ATCC 8461 as described in the section headed Bioassay I, is approximately 180 units per HAEA$_{308}$ unit.

PROPERTIES OF ANTIBIOTIC 890A$_5$

Antibiotic 890A$_5$ is an acidic substance which moves to the positive pole on electrophoresis at neutral pH.

The sodium salt is a white powder when lyophilized from aqueous solution.

The ultraviolet absorbance spectrum has maxima at 308.5 and 228 nm, and a minimum at 262 nm. The E% at 308.5 nm of a solution of the sodium salt of antibiotic 890A$_5$ in water at neutral pH is estimated to be 490 for a pure sample; the ratio of absorbances $A_{308}/A_{260}$ is 2.0 and the ratio $A_{308}/A_{228}$ is 1.03. More than 90% of the absorption at 308 nm may be eliminated by reaction with hydroxylamine, giving a product with an increased absorbance at 260 nm. The magnitude of the $A_{260}$ increase is approximately one-fourth of the $A_{308}$ decrease. The kinetics of the $A_{308}$ decrease under the conditions described for measuring the HAEA$_{308}$ appear to be first order, with a half-life at room temperature between 1 and 3 minutes.

The circular dichroism spectrum of 890A$_5$ has a positive maximum at 304 nm with a specific ellipticity of 7189 degree-ml. per decimeter-gram, a point of zero ellipticity at 257.5 nm, and a negative minimum at 220 nm with a specific ellipticity of −21,218 degree-ml. per decimeter-gram. In calculating these values, the concentration of 890A$_5$ is estimated from the absorbance at 308 nm using an E% vaue of 490 at that wavelength.

The following table lists the 100 MHz-NMR signals for 890A$_5$ sodium salt in D$_2$O relative to the internal standard DSS; chemical shifts are given in ppm and coupling constants in Hz; the apparent multiplicities are indicated.

1.29 (d, J=6.2, $\underline{CH_3}$—CH); 2.05 (S, CH$_3$C=O); 3.09 (app. d of d, C—$\underline{CH_2}$—C); 3.41 (d of d, J=5.0, 3.0, >$\underline{CH}$—C=O); 4.16 (m, >$\underline{CH}$—N and >$\underline{CH}$—OH); 6.00 and 7.11 (doublets, J=13.8, S—$\underline{CH}$=CH—N).

The antibiotic potency of 890A$_5$, measured on *Vibrio percolans* ATCC 8461, is 12 units per HAEA$_{308}$ unit.

Mass Spectral Analysis of 890A$_2$ and 890A$_5$

The mass spectral data for 890A$_5$ is obtained on tri-methylsilyl derivatives prepared from ammonium salts of the antibiotic with bis-trimethylsilyltrifluoro acetamide in dimethyl formamide. Conversion of the sodium salt of the antibiotic to the ammonium salts is carried out by using the ammonium salt of an acidic ion exchange resin.

Trimethyl-silylation of 890A$_2$ and 890A$_5$ results in three different derivatives: a di- and a tri-trimethylsilyl derivative (M.W.s 456 and 528, respectively) and a small amount of a tetra-trimethylsilyl derivative of a hydrolysed product (M.W. 618) wherein the β-lactam ring is open.

The values of the most important mass spectral fragments are given below:

di-trimethylsilyl derivative: 441; 299; 298 and 84; tri-trimethylsilyl derivative: 513; 371; and 156; tetra-trimethylsilyl derivative (only low-resolution signal observed): 618 and 603.

Antibiotics 890A$_2$ and 890A$_5$ are believed to be isomers having a molecular structure as follows:

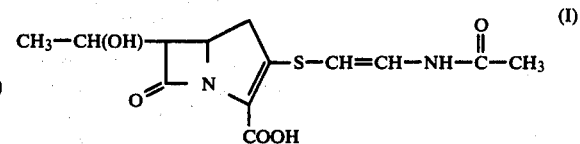

Antibiotics 890A$_2$ and 890A$_5$ are further characterized by the following antibiotic spectrum profiles.

The test to determine the antibiotic spectrum profile of antibiotic 890A$_2$ is carried out by saturating ¼ inch diameter paper discs in a solution of antibiotic 890A$_2$ in 5% methanol at a concentration of 5 μg./ml.; air drying the saturated paper discs and placing them on the surface of 100×15 mm. petri plates containing 5 ml. of seeded nutrient agar plus 0.2% yeast extract.

The test to determine the antibiotic spectrum profile of antibiotic 890A$_5$ is carried out by application of a 0.015 ml. droplet of a 33 μg./ml. aqueous solution of the antibiotic on the surface of a 100×15 mm. petri plate containing 5 ml. of seeded nutrient agar plus 0.2% yeast extract. The results, expressed in terms of the diameter in millimeters of the zone of inhibition, are set forth in Table III.

The spectra of antibiotic 890A$_2$ and 890A$_2$ are quite similar, except for the resistance of 890A$_5$ to inactivation by Difco penicillinase and by lactamase(s) produced by a cephalosporin C-resistant strain of *Vibrio percolans* (MB-2566). The results also indicate that antibiotic 890A$_2$ is markedly more potent than 890A$_5$.

TABLE III

In Vitro Antibacterial Spectrum Profile (ASP) of Antibiotics 890A$_2$ and 890A$_5$

| Organism | Merck No. | ATCC No. | Inhib. Zone Diam., mm 890A$_2$ - 5 μg./ml. | 890A$_5$ - 33 μg./ml. |
|---|---|---|---|---|
| *Bacillus sp.* | MB-633 | — | 40 | 18 |
| *Proteus vulgaris* | MB-1012 | — | 11 | 23 |
| *Pseudomonas aeruginosa* | MB-979 | — | 0 | 0 |
| *Serratia marcescens* | — | 990 | 23 | 29 |
| *Staphylcoccus aureus* | — | 6538 P | 34 | 34 |
| *Bacillus subtilis* | — | 6633 | 42 | 27 |
| *Sarcina lutea* | — | 9341 | 42 | 40 |
| *Staphylococcus aureus* | MB-698 | — | 30 | 35 |
| *Streptococcus faecalis* | MB-753 | — | 12 | 0 |
| *Alcaligenes faecalis* | — | 213 | 34 | 25 |
| *Brucella bronchissptica* | — | 4617 | 29 | 22 |
| *Salmonella gallinarum* | MB-1287 | — | 33 | 26 |
| *Vibrio percolans* | — | 8461 | 31 | 32 |
| *Xanthomonas vesicatoria* | MB-815 | — | 29 | 20 |
| *Proteus vulgaris* | — | 21100 | 30 | 27 |
| *Escherichia coli* | MB-1418 | — | 32 | 27 |
| *Pseudomonas stutzeri* | — | 11607 | 19 | 14 |
| *Klebsiella pneumoniae* | MB-1264 | — | 31 | 27 |
| *Aerobacter aerogenes* | MB-835 | 27 | 24 | |
| *Erwinia atroseptica* | — | 4466 | 26 | 21 |
| *Pseudomonas aeruginosa* | MB-2824 | — | 13 | 0 |
| *Corynebacterium pseudodiph.* | — | 9742 | 35 | 33 |
| *Escherichia coli* | — | 9637 | 29 | 24 |
| *Streptococcus faecium* | MB-2820 | — | 22 | 0 |
| *Streptococcus agalactiae* | MB-2875 | — | 32 | 27 |
| *Vibrio percolans* resistant to ceph. C) | MB-2566 | — | 11 | 35 |
| *Proteus vulgaris* (episome)$^a$ | MB-2112 | — | 33 | 23 |
| *Proteus mirabilis* | MB-3126 | — | 22 | 20 |
| *Staphylococcus aureus* (res. methicillin) | MB-2949 | — | 11 | 15 |
| *Vibrio percolans* +2 × 10$^5$ units/ml. penicillinase | MB-1272 | — | 7 | 40 |
| *Vibrio percolans* + Aerobacter | | | | |

TABLE III-continued

In Vitro Antibacterial Spectrum Profile (ASP) of Antibiotics 890A$_2$ and 890A$_5$

| | | | Inhib. Zone Diam., mm | |
|---|---|---|---|---|
| Organism | Merck No. | ATCC No. | 890A$_2$ - 5 µg./ml. | 890A$_5$ - 33 µg./ml. |
| Lactamase | MB-1272 | — | 31 | 36 |

[a]this episome confers resistance to tetracycline, chloramphenicol, kanamycin and streptomycin at a concentration of 20 µg./ml. and neomycin at a concentration of 25 µg./ml. and sulfa drugs.

Antibiotic 890A$_2$ exhibits in vivo activity against gram-negative and gram-positive organisms and hence is useful in controlling bacterial infections in animals and humans. In determining the in vivo activity, antibiotic 890A$_2$ is dissolved in 0.15 M NaCl, 0.01 M sodium phosphate, pH 7.0, and diluted with water to provide five fourfold concentrations of drug for testing. Female white Swiss mice, averaging about 21 g. in weight, were infected intraperitoneally with the test organism suspended in broth. The numbers of organisms injected were determined by standard plate-count techniques. At the time of infection and again 6 hours later, certain of the mice were treated intraperitoneally with the antibiotic. Five mice were used for each concentration of drug tested. An additional two mice, not infected, were treated with the antibiotic to determine whether the amount of agent injected was toxic. Controls of five mice for each of several dilutions of the infecting culture were included in each test in order to calculate the numbers of organisms that were lethal to 50% of the infected, untreated mice (LD$_{50}$). This calculation was made using survival data of the seventh day after infection, at which time the amount of drug that should protect 50% of the infected mice (ED$_{50}$) also was calculated.

All animals receiving this challenge and not treated with antibiotic died within 48 hours of the infection. The efficacy of antibiotic 890A$_2$, having a potency of 59 units/ml., against *Salmonella schottmuellari* MB-2837 is set forth below:

| Units/ml.[a] | Route | ED$_{50}$ × 2 doses Units |
|---|---|---|
| 59 | ip | 19 |

Antibiotics 890A$_2$ and 890A$_5$ are valuable antibiotics active against various gram-positive and gram-negative bacteria and, accordingly, find utility in human and veterinary medicine. The compounds of this invention can be used alone or in combination with each other as antibacterial drugs for treating infections caused by gram-positive or gram-negative bacteria, for example, against *Staphylococcus aureus*, *Proteus mirabilis*, *Escherichia coli*, *Klebsiella pneumoniae* and *Salmonella schottmuellari*. The antibacterial materials of the invention may further be utilized as additives to animal feedingstuffs, for preserving foodstuffs and as disinfectants. For example, they may be employed in aqueous compositions in concentrations ranging from about 0.1 to about 100 parts of antibiotic per million parts of solution or preferably in concentrations ranging from about 1 to about 10 parts of antibiotic per million parts of solution in order to destroy and inhibit the growth of harmful bacteria on medical and dental equipment and as bactericides in industrial applications, for example in water-based paints and in the white water of paper mills to inhibit the growth of deleterious bacteria.

The antibiotics of this invention may be used in any one of a variety of pharmaceutical preparations as the sole active ingredients or in combination either with one or more other antibiotics or with one or more pharmacologically active substances. As an example of the former, an aminocyclitol antibiotic such as gentamicin may be coadministered in order to minimize any chance that resistant organisms will emerge. As an example of the latter, diphenoxylate and atropine may be combined in dosage forms intended for the therapy of gastroenteritis. The antibiotics may be employed in capsule form or as tablets, powders or liquid solutions or as suspensions or elixirs. It may be administered orally, topically, intravenously or intramuscularly. Furthermore the antibiotics 890A$_2$ and 890A$_5$ may be used in combination with each other.

Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In veterinary medicine, such as in the treatment of chickens, cows, sheep, pigs and the like, the composition may, for example, be formulated as an intramammary preparation in either long acting or quick-release bases.

The dosage to be administered depends to a large extent upon the condition of the subject being treated, the weight of the host and the type of infection, the route and frequency of administration, the parenteral route being preferred for generalized infections and the oral route for intestinal infections.

In the treatment of bacterial infections in man, the compounds of this invention are administered orally or parenterally, in accordance with conventional procedures for antibiotic administration, in an amount of from about 2 to 600 mg./kg./day and preferably about 5 to 100 mg./kg./day in preferably divided dosage, e.g. three to four times a day. They may be administered in dosage units containing, for example, 100, 330, 400 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use, all of such adjustments being within the skill of the practitioner in the field.

Included in this invention are the non-toxic, pharmaceutically acceptable salts of 890$A_2$ and 890$A_5$ for example, the pharmacologically acceptable salts formed with inorganic and organic bases; which include, for example, metal salts derived from alkali metal or alkaline earth metal hydroxides, carbonates or bicarbonates such as those derived from sodium, potassium, ammonium and calcium and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino and guanidino-substituted lower alkanoic acids and nitrogen-containing heterocyclic amines. Representative examples include salts derived from sodium hydroxide, ammonium hydroxide, sodium carbonate, sodium bicarbonate, potassium carbonate, potassium hydroxide, calcium carbonate, trimethylamine, triethylamine, piperidine, N-ethylpiperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The salts of the compounds of the present invention may be prepared by conventional methods well known in the art. For example, the mono-salts such as monosodium salt obtained by treating one equivalent of sodium hydroxide with one equivalent of the product (I) in a suitable solvent. Also mixed salts with divalent cations may be prepared by combining one mole of a divalent base with one mole of the product (I) plus one equivalent of another acid. Alternatively, salts may be obtained by treating one equivalent of a base having a divalent cation, such as calcium hydroxide, with one equivalent of the product (I). The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

Fermentation broths containing the antibiotics 890$A_2$ and 890$A_5$ produced in accordance with the procedures described herein have activities ranging from about 2 to 170 units per ml. when assayed in accordance with the disc-diffusion assay using *Vibrio percolans* (ATCC 8461). The antibiotics 890$A_2$ and 890$A_5$ contained in these fermentation broths can be recovered and purified by a number of procedures. One such procedure comprises adsorbing the antibiotics 890$A_2$ and 890$A_5$ on a strongly basic anion exchange resin. Illustrative of such strongly basic anion exchange resins are those having a styrene-divinylbenzene matrix, for example the polystyrene nuclear quaternary ammonium resin Dowex 1×2 (manufactured by Dow Chemical Co., Midland, Michigan), on the chloride cycle. Other representative members of this class of strongly basic exchange resins include the following: Duolite A-40, A-42, A-101, A-102 and A-114 (manufactured by Chemical Process Co., Redwood City, California). Amberlite IRA-400, IRA-401 and IRA-410. Alternately, a weekly basic anion exchange resin such as Amberlite IRA-68 may be used. (Amberlite resins are manufactured by Rohm and Haas, Washington Square, Philadelphia 5, Penn.)

The adsorbed antibiotic is readily eluted from the anion exchange resin with salt solutions in 50% (v/v) aqueous methanol. The eluate so obtained can be further purified, if desired, by other purification procedures. Thus, the eluate can be purified by concentrating it and passing it through a column packed with an acrylic ester polymer of intermediate polarity such as XAD-7 or 8 or through a column packed with a polystrene, non-polar, hydrophobic crosslinked divinyl benzene polymer such as XAD-1, 2 and 4, preferably XAD-2. (XAD-1, 2, 4, 7, and 8 are manufactured by Rohm and Haas, Washington Square, Philadelphia 5, Pennsylvania). This process partially resolves the antibiotics 890$A_2$ and 890$A_5$. The fractions rich in 890$A_2$ and those rich in 890$A_5$ are pooled. These pooled fractions are further purified.

A method of obtaining further purified antibiotic 890$A_2$ and 890$A_5$ is by the use of gel filtration through polyacrylamide gel having a pore size which excludes molecules having a molecular weight greater than 1800, such as Bio-Gel P-2 (manufactured by Bio.Rad, Richmond, California). Other gels, such as Sephadex G-10 may also be employed for desalting.

The preferred procedure by which antibiotics 890$A_2$ and 890$A_5$ may be obtained in high purity from a broth consists of a centrifugation or filtration of the broth to remove solids; an adsorption and elution of the filtrate from an anion-exchange resin such as Dowex-1×2 in the chloride cycle with 3% NaCl in 50% (v/v) aqueous methanol, which both concentrates and partially purifies the antibiotics; a passage over a column of suitably prepared XAD-2, which retards the antibiotics and thereby purifies and desalts the Dowex-1×2 eluate. Furthermore, the antibiotic 890$A_5$ is retarded more than the antibiotic 890$A_2$ and thereby the two antibiotics are partially resolved. The fractions enriched in 890$A_2$ and 890A$_5$ are pooled and further purified. Chromatography on a Dowex-1×2 minus 400 mesh resin, with elution by NaCl and/or NH$_4$Cl in 50% aqueous methanol, gives a product free from most UV-absorbing impurities (the NH$_4$Cl is used to provide some buffering capacity in the eluent); and a desalting on Bio-Gel P-2 or Sephadex G-10, removes most of the salt introduced in the Dowex-1×2 chromatography.

When broths of low potency are treated by the above procedure, the final material may have significant quantities (more than 50%) of impurities remaining. These impurities may be reduced by an additional cycle of chromatography on Dowex-1×2, minus 400 mesh, with elution by a solution containing sodium chloride and 50% isopropanol. It is also advisable, when isolating antibiotic from low-potency broths, to do a second stage of XAD-2 chromatography. This provides additional purification, removes residual salt, and partially resolves the antibiotic 890A$_2$ from 890A$_5$. Specifically, the 890A$_5$ elutes later than the 890A$_2$ and the two may be distinguished by their different ratios of bioactivity to HAEA$_{308}$. Those fractions which demonstrate a ratio of bioactivity on *Vibrio percolans* ATCC 8461 to HAEA$_{308}$ of 180 bioactivity units per HAEA$_{308}$ unit contain antibiotic 890A$_2$ and those fractions which demonstrate a ratio of bioactivity on *Vibrio percolans* ATCC 8461 to HAEA$_{308}$ of 12 bioactivity units per HAEA$_{308}$ unit contain antibiotic 890A$_5$.

In purification by column chromatography, in general only those fractions of the eluted volume which contain antibiotic at least 30% as pure as the purest fraction are combined for further purification. Criteria of purity are the ratios bioactivity/A$_{220}$, A$_{308}$/A$_{260}$ and HAEA$_{308}$/A$_{220}$; and, in desalting procedures, the coductivity. Thus at each chromatography step the A$_{220}$, A$_{260}$, A$_{308}$ and bioactivity of appropriate fractions are measured. Where possible, HAEA$_{308}$ is also measured, and in desalting, conductivities are measured. The criteria for deciding which fractions to combine for subsequent operations may be adjusted somewhat to achieve a higher yield, at the expense of purity, or conversely a higher purity at the expense of yield.

In laboratory-scale operations (less than 20 liters of sample volume), all chromatography steps except the XAD-2 chromatography are carried out in a cold room at 2°–5° C. The XAD-2 chromatography is carried out at room temperature unless stated otherwise. The pH of antibiotic solutions to be stored is adjusted to 7–8 by careful addition of dilute NaOH or HCl solutions. Aqueous solutions are stored in a refrigerator, or preferably in ice water, and 50% methanol solutions are stored at −20° C.

At stages of purification prior to XAD-2 chromatography, solutions are generally brought to 25 $\mu$M in EDTA by addition of 1/4000th volume of a solution of 0.1 M Na$_2$ EDTA which has been neutralized to pH 7.0 by addition of sodium hydroxide (0.1 M "neutral EDTA")

A flow sheet diagram of the purification procedure for obtaining antibiotics 890A$_2$ and 890A$_5$ is presented in FIGS. 1 and 2, respectively.

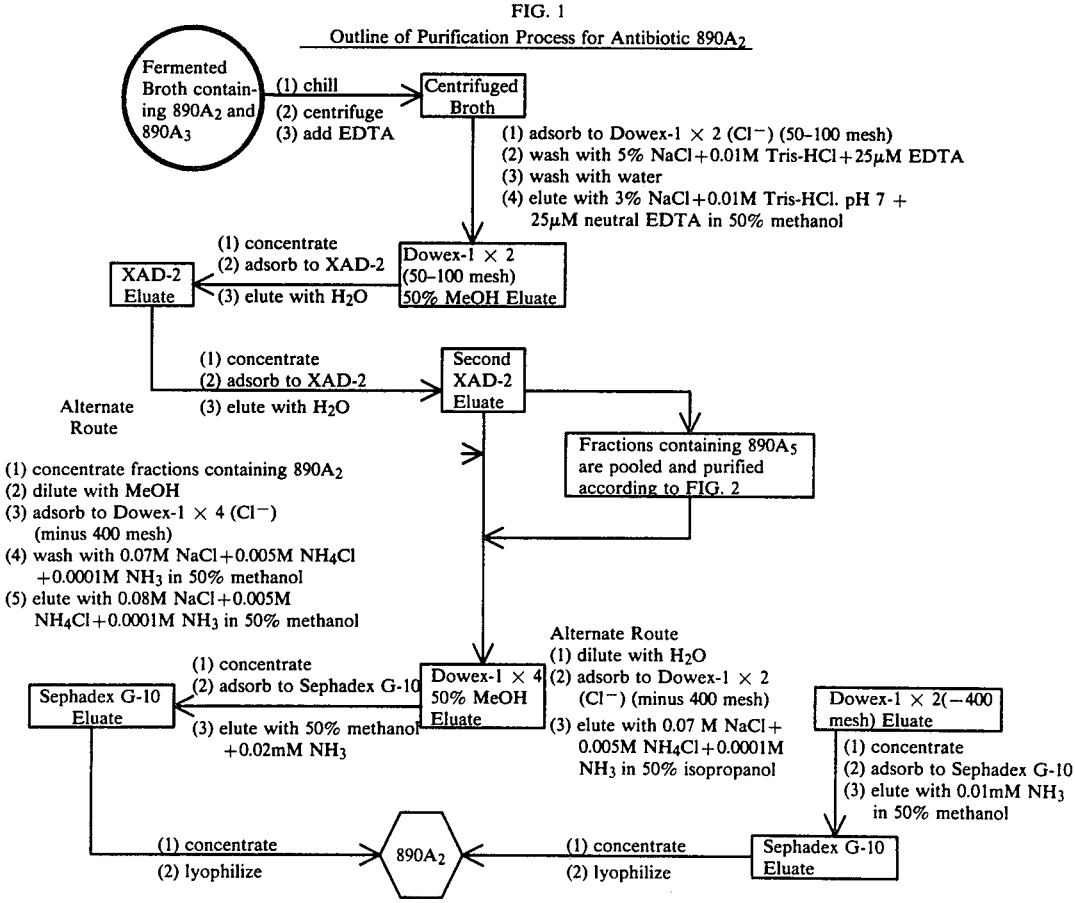

FIG. 1 Outline of Purification Process for Antibiotic 890A$_2$

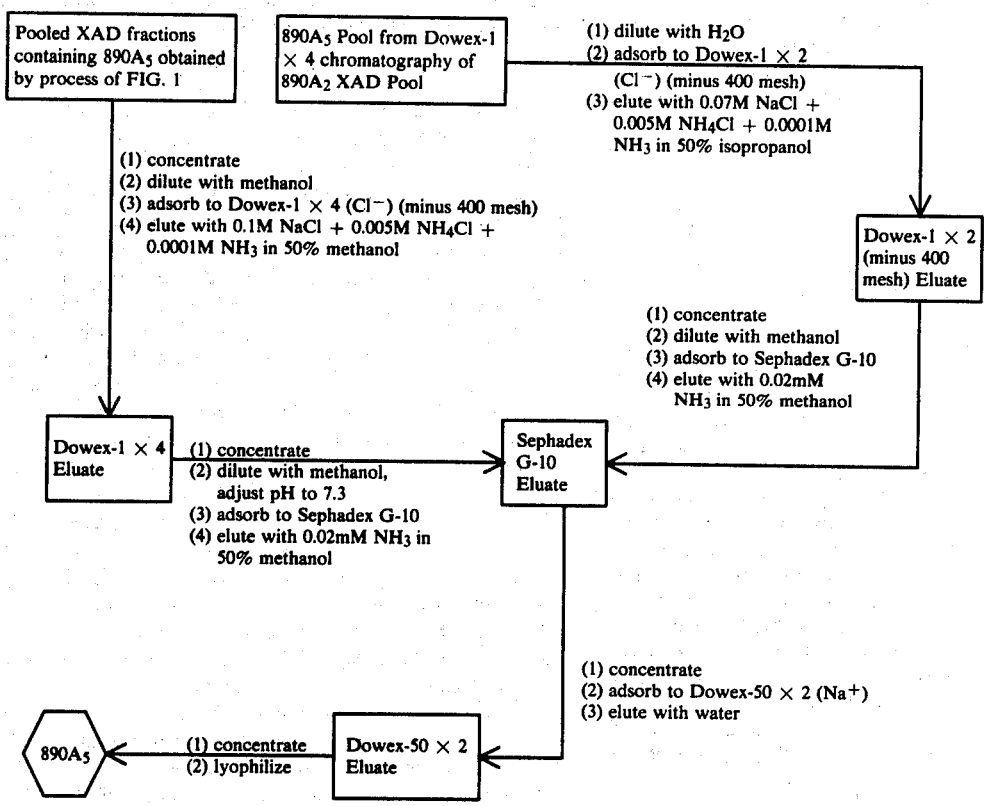

FIG. 2
Outline of Purification Process for Antibiotic 890A$_5$

ASSAY PROCEDURES FOR ANTIBIOTICS 890A$_2$ AND 890A$_5$

I. Bioassay

An agar plate disc-diffusion method is employed using either *Vibrio percolans* ATCC 8461 or *Salmonella callinarum* MB-1287 as tester organism. A purified sample of antibiotic 890A$_1$ is used as standard. Antibiotic 890A$_1$ is prepared according to the procedure set forth in Example 5.

Plates containing *Vibrio percolans* ATCC 8461 are prepared as follows:

A lyophilized culture of Vibrio percolans ATCC 8461 is suspended in 15 ml. of a sterilized medium containing 8 g./liter of Difco Nutrient Broth and 2 g./liter of yeast extract in distilled water "nutrient broth-yeast extract" (herein after designated NBYE). The culture is incubated overnight on a rotary shaker at 28° C. This culture is used to inoculate the surface of slants containing 1.5% agar in NBYE, and the inoculated slants are incubated overnight at 28° C., and then stored in a refrigerator.

The refrigerated slants prepared from a single lyophilized culture are used for up to four weeks from their preparation, as follows: A loop of inoculum from the slant is dispersed in 50 ml. of NBYE contained in a 250 ml. Erlenmeyer flask. The culture is incubated overnight on a rotary shaker at 28° C. and then diluted to a density giving 50% transmittance at 660 nm. A 33.2 ml. portion of this diluted culture is added to 1 liter of NBYE containing 15 g. of agar and maintained at 46° C. The inoculated agar-containing medium is poured into 100×15 mm. plastic petri dishes, 5 ml. per dish, chilled, and maintained at 2°-4° C. for up to 5 days before using.

Plates containing *Salmonella gallinarum* MB-1287 are prepared as follows:

A sealed tube containing *Salmonella gallinarum* MB-1287 cells in skim milk, which had been frozen and lyophilized and sealed under vacuum, is opened and inoculated into 15 ml. of Brain Heart Infusion broth. The cells are allowed to grow without shaking at 37° C. overnight, and the culture is inoculated onto slants of 0.8% BBL Nutrient broth +0.2% Difco yeast extract +1.5% agar. After growth overnight at 37° C., a loop of the culture is transferred from the slant to a flask containing 50 ml. of 0.8% nutrient broth +0.2% yeast extract. The flask is shaken overnight, and 20 ml. of this culture is inoculated into one liter of 0.8% nutrient broth +0.2% yeast extract +1.5% agar which had been sterilized and cooled to 48° C. The inoculated NBYE agar is poured immediately into 100×15 mm. plastic petri dishes, 5 ml. per dish, and the plates are kept at 2°-4° C. until use.

Filter paper discs of one-half inch diameter are dipped into the solution to be assayed, and are placed on the agar. Alternatively, the discs may be loaded by pipetting one-tenth ml. of solution onto a dry disc, and then placing the disc on the agar. The diameter of the zone of inhibition is measured after appropriate incubation (9-18 hours at 37° C. for *Salmonella gallinarum* MB-1287 or 12-24 hours at 25° C. for *Vibrio percolans* ATCC 8461.) If necessary, dilutions of the solutions to be assayed are made in 0.05 M potassium phosphate buffer, pH 7.4 "potassium phosphate buffer" (hereinafter referred to as KPB), or in deionized water.

Calculations of potencies proceed as follows: a slope is determined by measuring the zone diameters of a solution of antibiotic 890A$_2$ or 890A$_5$ and of a fourfold dilution (in KPB) of this solution. Two discs of each concentration are assayed on a single plate, and the average zone size at each concentration is determined. The slope is equal to one-half of the difference of the average zone sizes. Potencies are then calculated by the formula:

Potency (units/ml.) =

$$\left( \frac{[D - D_s] \log 2}{\text{slope}} \right)$$

(Potency of Standard) × Dilution × 10 where D is the average diameter of the zones formed by the unknown, $D_s$ is the average diameter of the standard zones, and "Dilution" is the degree to which the unknown was diluted before assay. If no standard is used, $D_s$ is assumed to be 25 mm. and (Potency of Standard) is taken as 1 unit/ml., when measured on *Vibrio percolans* ATCC 8461. Pure 890A$_1$ is defined as having a potency of 250 units per hydroxylamine-extinguishable absorbance unit at 300 nm, when used as a standard.

For assays on *Salmonella gallinarum* MB-1287 plates, a slope is determined in the same way as on *Vibrio percolans* ATCC 8461 plates. When no standard is used, only relative potencies are calculated. If no slope is measured, a value of 2.3 mm. is assumed. The potency calculations proceed as with the *Vibrio percolans* ATCC 8461 assay. If no 890A$_1$ standard is used, a control of penicillin G at 250μ g/ml. may be employed in order to verify that the sensitivity of the organisms is in the normal range.

II. Assay Procedure for Determining "890 Assay Units"

A conventional agar plate disc-diffusion method is employed using *Vibrio percolans* ATCC 8461 as tester organism. Cephaloridine is employed as a standard. Plates containing *Vibrio percolans* ATCC 8461 are prepared as follows. A culture of *Vibrio percolans* ATCC 8461 is incubated in nutrient broth-yeast extract overnight on a rotary shaker at 28° C. and then diluted to a density of 60% transmittance at 660 nm. A 33.2 ml. portion of this diluted culture is added to 1 liter of a medium composed of nutrient agar plus 0.2% yeast extract maintained at 46° C. The inoculated agar-containing medium is poured into 100×15 mm. plastic-petri dishes, 10 ml. per dish, chilled, and maintained at 2°–4° C. for up to 5 days before use.

The concentration of cephaloridine which is equivalent to 1 unit/ml. of 890A is determined by assay on plates prepared as above, but containing 5 ml. of inoculated medium per plate, as follows. Four concentrations of cephaloridine constitute the standard—3.12, 6.25, 12.5 and 25 mcg per ml. with the 12.5 mcg per ml. as a reference solution. The zone diameters on a 5 ml. plate for the standard are as follows:

| Conc. (mcg/ml.) | Zone Diameter (mm.) |
|---|---|
| 3.12 | 16.8 |
| 6.25 | 22.3 |
| 12.5 | 25.0 |
| 25 | 29.6 |

A unit is defined as the amount of antibiotic per ml. producing a 25 mm. zone of inhibition on a 5 ml. plate as described in section I above. Therefore, in this assay a concentration of 12.5 mcg per ml. of cephaloridine is considered equivalent to 1 unit of 890A per ml. Since the slope of the line for cephaloridine is 4.0 calculations of the potency of a sample are made using a slope of 4.0.

III. Hydroxylamine Reaction

Both antibiotics 890A$_2$ and 890A$_5$ react with hydroxylamine and produce a substance with greatly diminished absorbance at 308 nm. This provides the basis for a quantitative assay of the antibiotics 890A$_2$ and 890A$_5$.

The solution to be assayed is brought to 0.05 M in potassium phosphate, pH 7.4 by adding 1/20th volume of a solution containing 0.8 M K$_2$HPO$_4$ and 0.2 M KH$_2$PO$_4$. Then one-hundredth volume of 1 M hydroxylamine hydrochloride is added, and the absorbance at 308 nm is measured at intervals of one-half to two minutes. The reaction is conducted at room temperature. First-order kinetics are assumed and a half-life is estimated from the absorbance decrease during the first ten minutes. From this half-life, the time is estimated beyond which no further absorbance decrease should be observed and observations are continued beyond that time. If no further decrease is observed beyond that time, the total absorbance decrease (correcting for dilution effect and absorbance of the hydroxylamine) is taken as the "Hydroxylamine-extinguishable absorbance at 308 nm (HAEA$_{308}$)". If absorbance decrease is observed beyond that time, the rate of background absorbance decrease is calculated, and the observed decrease at that time is corrected for background decrease, assuming that background decrease is linear with time. The corrected value is then recorded as the HAEA$_{308}$.

The number of HAEA$_{308}$ units is equal to the HAEA$_{308}$ multiplied by the volume in ml.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of the products of this invention should be construed as constituting an analogous method. The described processes are capable of wide variation and modification and any minor departure or extension is considered as being within the skill of the artisan and as falling within the scope of this invention.

EXAMPLE 1

Production of Mixture Containing Antibiotic 890A$_2$ and 890A$_5$

A tube of lyophilized culture of *Streptomyces flavogriseus* MA-4434 is opened aseptically and the contents suspended in a tube containing 0.8 ml. sterile Davis salts solution having the following composition:

| Davis Salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |

-continued

| Davis Salts | |
|---|---|
| Distilled H₂O | 1000 ml. |

This suspension is used to inoculate 4 slants of sterile medium A having the following composition:

| Medium A | |
|---|---|
| Dextrose | 10.0 g. |
| Piptone | 5.0 g. |
| Yeast Extract | 3.0 g. |
| NaCl | 12.705 g. |
| KCl | 0.72 g. |
| FeSO₄(NH₄)₂SO₄ . 6H₂O | 0.0351 g. |
| MgCl₂ . 6H₂O | 5.32 g. |
| CaCl₂ . 2H₂O | 0.728 g. |
| Distilled H₂O | 1000 ml. |
| pH 7.4 (before sterilization) | |
| Agar | 25.0 g. |

The inoculated slants are incubated for one week at 27°–28° C. and then stored at 4°–6° C. until used 10 days later. A one-half portion of the surface growth of one of these slants is used to inoculate baffled 250 ml. Erlenmeyer flasks containing 50 ml. of medium B having the following composition:

| Medium B | |
|---|---|
| Yeast Autolysate (+Ardamine) | 10.0 g. |
| Glucose | 10.0 g. |
| Phosphate Buffer* | 2.0 ml. |
| MgSO₄ . 7H₂O | 50 mg. |
| Distilled H₂O | 1000 ml. |
| pH: adjust to 6.5 using HCl or NaOH | |
| +Ardamine: Yeast Products Corporation | |
| *Phosphate Buffer solution | |
| KH₂PO₄ | 91.0 g. |
| Na₂HPO₄ | 95.0 g. |
| Distilled H₂O | 1000 ml. |

Three seed flasks are inoculated to provide sufficient inoculum for the 12 two liter production flasks fermented in this batch. The seed flasks are shaken for one day at 28° C. on a 220 rpm shaker (2″ throw). The flasks are removed from the shaker and stored for one day at 4° C. The contents of these seed flasks are used to inoculate 12 two liter unbaffled Erlenmeyer production flasks (7 ml. of inoculum per flask) containing 250 ml. of the production medium C having the following composition:

| Medium C | |
|---|---|
| Tomato Paste | 20.0 g. |
| Primary Yeast | 10.0 g. |
| Dextrin (Amidex) | 20.0 g. |
| Deionized H₂O | 1000 ml. |
| pH adjust to 7.3 using NaOH | |

After inoculation, production flasks are incubated at 24° C. with agitation on a 220 rpm shaker (2″ throw) for four days and five hours. At the end of this period flasks are harvested and assayed for activity by using standard *Salmonella gallinarum* MB1287 and *Vibrio percolans* ATCC 8461 assay plates using ½ inch assay discs dipped into centrifuged broth samples. The results are tabulated below:

| Assay at Harvest | |
|---|---|
| Harvest age (hours) | 101 |
| pH | 7.1 |
| *Salmonella gallinarum* (mm. zone) | 31 |
| *Vibrio percolans* (mm. zone) | 43 |

The fermentation broth is centrifuged. To the clear centrifugate, 2.2 l., at pH 6.8, is added 22 mg. of (ethylenedinitrilo)tetraacetic acid and the pH is adjusted to 7.2. The pH adjusted centrifugate is adsorbed on 150 ml. of Dowex 1×2 resin in the Cl⁻ cycle at 15 ml./min. collecting the spent stream as one fraction. The adsorbate is washed with 150 ml. of deionized water containing 10μ g./ml. of (ethylenedinitrilo)tetraacetic acid and then washed with 5% NaCl containing 10μ g./ml. of (ethylenedinitrilo)tetraacetic acid collecting 5×75 ml. fractions.

The 5% NaCl eluting solution is followed by a 60 ml. displacement wash of deionized water and then the antibiotics 890A₂ and 890A₅ are eluted with 90% (v/v) methanol; 3% ammonium chloride (w/v/); 10% water (v/v) containing 10 μg./ml. (ethylenedinitrilo) tetraacetic acid, collecting 5×75 ml. fractions. Fractions were assayed against *Vibrio percolans*, ATCC 8461 and the results are tabulated below as percent of starting bioactivity:

| Fraction | Recovery |
|---|---|
| Feed | 100% |
| Spent | 0 |
| Water displacement wash | 1% |
| MeOH/NH₄Cl eluates fractions | |
| 1 to 3 | 24% |

EXAMPLE 2

Shake Flask Production of Antibiotic 890A₂

A tube of lyophilized culture of *Streptomyces flavogriseus* MA-4434 is opened aseptically and the contents suspended in a tube containing 0.8 ml. of sterile Davis salts having the following composition:

| Davis Salts | |
|---|---|
| Sodium citrate | 0.5 g. |
| K₂HPO₄ | 7.0 g. |
| KH₂PO₄ | 3.0 g. |
| (NH₄)₂SO₄ | 1.0 g. |
| MgSO₄ . 7H₂O | 0.1 g. |
| Distilled H₂O | 1000 ml. |

This suspension is used to inoculate four slants of sterile medium A having the following composition:

| Medium A | |
|---|---|
| Glycerol | 20.0 g. |
| Primary Yeast | 5.0 g. |
| Fish Meal | 15.0 g. |
| Distilled H₂O | 1000 ml. |
| Agar | 20.0g. |
| pH: adjust to 7.2 using NaOH | |

The inoculated slants are incubated for one week at 27°–28° C. and then stored at 4°–6° C. until used (not longer than 21 days).

A one-third portion of the growth from one slant is used to inoculate one baffled 250 ml. Erlenmeyer flask. A total of four slants are used to inoculate twelve flasks. Each flask contains 50 ml. of medium B having the following composition:

| Medium B | |
|---|---|
| Yeast Autolysate (+Ardamine) | 10.0 g. |
| Glucose | 10.0 g. |
| Phosphate Buffer* | 2.0 ml. |
| $MgSO_4 \cdot 7H_2O$ | 50.0 mg. |
| Distilled $H_2O$ | 1000 ml. |
| pH: adjust to 6.5 using HCl or NaOH | |
| +Ardamine: Yeast Products Corporation | |
| *Phosphate Buffer solution | |
| $KH_2PO_4$ | 91.0 g. |
| $Na_2HPO_4$ | 95.0 g. |
| Distilled $H_2O$ | 1000 ml. |

The seed flasks are shaken for one day at 27°–28° C. on a 220 rpm shaker (2" throw). The flasks and contents are stored stationary for one day at 4° C.

Forty-four 2 liter Erlenmeyer production flasks, each containing 200 ml. of medium C, are inoculated with 8 ml. per flask of the growth from the seed flasks. The medium C has the following composition:

| Medium C | |
|---|---|
| Tomato Paste | 20.0 g. |
| Primary Yeast | 10.0 g. |
| Dextrin (Amidox) | 20.0 g. |
| $CoCl_2 \cdot 6H_2O$ | 5.0 mg. |
| Distilled $H_2O$ | 1000 ml. |
| pH: adjust to 7.2–7.4 using NaOH | |

After inoculation, the production flasks are incubated at 24° C., with agitation on a 212 rpm shaker (2" throw), for four days and five hours. The flasks are harvested and assayed for activity by using standard *Salmonella gallinarum* MB1287 and *Vibrio percolans* ATCC 8461 assay plates using ½ inch assay discs dipped into centrifuged broth samples. Samples are diluted with 0.02 M phosphate buffer, pH 7.0 when necessary. The results are tabulated below:

| Harvest Age Hours | 101 |
|---|---|
| pH | 7.2 |
| *Salmonella gallinarum* (mm zone) | 35 |
| *Vibrio percolans* 1/10 dil (mm zone) | 25 |
| 890 Assay Units | 121 |

The total of 7.0 liters of whole broth obtained from this fermentation is chilled to 3° C. and centrifuged in 200 ml. portions at 9000 rpm for 15 minutes each. To the combined supernatant is added 1.7 ml. of 0.1 M neutral EDTA and the batch is held at 3° C.

The above fermentation is repeated under identical conditions with the exception that the 44 two liter Erlenmeyer production flasks are inoculated with 7 ml. per flask with growth from the seed flasks. The pH and assay results are tabulated below:

| Harvest Age Hours | 101 |
|---|---|
| pH | 7.3 |
| *Salmonella gallinarum* (mm zone) | 38 |
| *Vibrio percolans* 1/10 dil (mm zone) | 27 |
| 890 Assay Units | 92.8 |

The total of 7.4 liters of whole broth obtained from this fermentation is chilled to 3° C. and centrifuged in 200 ml. portions at 9000 rpm for 15 minutes each. To the combined supernatant is added 1.8 ml. of 0.1 M neutral EDTA.

The supernatants from the centrifuged broths resulting from the two above fermentations in this Example are combined to give a total volume of 10 liters and a potency of 80 units/ml. by assay on *Vibrio percolans* ATCC 8461.

The combined supernatant is passed through a column of Dowex-1×2 (Cl−), 50–100 mesh, with bed dimensions 4.7 cm.×50 cm., at a flow rate of 60 ml. per minute. The column is washed with 1 liter of deionized water, and is eluted with 5 liters of 5% (w/v) NaCl solution containing 0.01 M Tris-HCl buffer, pH 7.0, and 25 $\mu$M neutral EDTA, at a flow rate of 50 ml. per minute.

The column is washed with 500 ml. of deionized water, and the antibiotics 890$A_2$ and 890$A_5$ are eluted with 2 liters of 3% NaCl+0.01 M Tris-HCl, pH 7.0, +25 $\mu$M neutral EDTA in 50% methanol, at a flow rate of 40 ml./minute. Fractions of 220 ml. are collected.

Antibiotic activity, as judged by assay on *Salmonella gallinarum* MB1287, appears in fractions 4 through 8, with a maximum in fraction 5. Fractions 4 through 8 contain 9% of the initial activity present in broth.

Fractions 4 through 7 are combined, concentrated to 150 ml. by rotary evaporation under reduced pressure, and diluted to 350 ml. by addition of 200 ml. of deionized water. The sample is applied to a column (5 cm.×25 cm.) of XAD-2, which had been washed previously with 3 liters each of 60% (v/v) acetone, deionized water and 5% (w/v) NaCl. The column is eluted with 500 ml. of deionized water at 20 ml./minute followed by 500 ml. of 60% (v/v) aqueous acetone. Fractions of 160 ml. each are collected. Antibiotic activity, determined by assay on *Salmonella gallinarum* MB1287, appears in fractions 1 through 5, with a maximum in fractions 3 and 4.

Fraction 4, the first acetone-containing fraction is concentrated to 10 ml. under reduced pressure, and diluted with 90 ml. of deionized water. This sample is applied to a column (5 cm.×25 cm.) of XAD-2, which had been washed previously with 3 liters each of 60% (v/v) acetone, deionized water and 5% (w/v/) NaCl. The column is eluted with deionized water at a flow rate of 20 ml. per minute. Fractions of from 140 to 190 ml. are collected. Antibiotic activity, determined by assay on *Salmonella gallinarum* MB1287, appears in fractions 2 through 7 with a maximum at fraction 4. Fractions 3, 4 and 5 are combined and added to fraction 3 from the XAD column described in the previous paragraph. The combined fractions contain 26,400 bioassay units, determined by assay on *Vibrio percolans* ATCC 8461, equal to 2.5% of the starting activity.

The combined XAD-2 fractions 3, from the first XAD column, and fractions 3, 4 and 5 from the second XAD column are concentrated under reduced pressure to 25 ml. and then 25 ml. of deionized water and 50 ml. of methanol are added. The methanolic solution is adsorbed to a column (2.15×26.4 cm.) of Dowex-1×4 (Cl$^-$), minus 400 mesh, which had been equilibrated with 50% aqueous methanol (v/v). The column is eluted with 1.44 liters of 0.07 M NaCl+0.005 M NH$_4$Cl+0.0001 M NH$_3$ in 50% methanol, at a flow rate of 2 ml. per minute. Fractions of 12.1 ml. are collected. The elution is continued with 2 liters of 0.08 M NaCl+0.005 M NH$_4$Cl+0.0001 M NH$_3$ in 50% methanol, collecting fractions of 11.7 ml. each.

A peak of UV absorbance at 300 nm appears in fractions 138 through 162, with a maximum at fractions 149–150. The absorption at 305 nm is observed to be extinguishable to the extent of 77% by reaction with L-cysteine at neutral pH. Fractions 145 through 155, containing antibiotic 890A$_2$, are pooled and concentrated to 2.4 ml., containing a total of 70.5 A$_{300}$ units.

The concentrated sample is applied to a column (2.2×70 cm.) of Bio-Gel P-2, 200–400 mesh, which had been washed with one liter of deionized water. The sample is allowed to drain to bed level, and the residue is washed in with two rinses of 1 ml. each of deionized water. The column is eluted with deionized water at the rate of 1 ml. per minute. Fractions of 2 to 3.5 ml. are collected.

The main peak of absorbance at 308 nm appears in fractions 64 to 72, immediately preceding and not completely resolved from the sodium chloride. Fractions 66 and 67 are combined, containing 27 absorption units of antibiotic 890A$_2$ at 308 nm and from 29 to 43 mg. of NaCl (as estimated by conductivity). These combined fractions were concentrated to 1.5 ml. under reduced pressure and lyophilized, giving 43.7 mg. of solids.

EXAMPLE 3

Preparation of Antibiotics 890A$_2$ and 890A$_5$

A tube of lyophilized culture of *Streptomyces flavogriseus* MA-4434 is opened aseptically and the contents suspended in a tube containing 0.8 ml. of sterile Davis salts having the following composition:

| Davis Salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of medium A having the following composition:

| Medium A | |
|---|---|
| Glycerol | 20.0 g. |
| Primary Yeast | 5.0 g. |
| Fish Meal | 15.0 g. |
| Distilled H$_2$O | 1000 ml. |
| Agar | 20.0 g. |
| pH: adjust to 7.2 using NaOH | |

The inoculated slants are incubated for one week at 27°–28° C. and then stored at 4°–6° C. until used (not longer than 21 days).

Ten ml. of medium B having the composition:

| Medium B | |
|---|---|
| Yeast Autolysate ($^+$Ardamine) | 10.0 g. |
| Glucose | 10.0 g. |
| Phosphate Buffer* | 2.0 ml. |
| MgSO$_4$ . 7H$_2$O | 50 mg. |
| Distilled H$_2$O | 1000 ml. |
| pH: adjust to 6.5 using HCl or NaOH | |
| $^+$Ardamine: Yeast Products Corporation | |
| *Phosphate Buffer solution | |
| KH$_2$PO$_4$ | 91.0 g. |
| Na$_2$HPO$_4$ | 95.0 g. |
| Distilled H$_2$O | 1000 ml. | is transferred aseptically to one of these slants, the spores and aerial mycelia scraped into suspension, and 3.3 ml. of this suspension used to inoculate a 2 liter baffled Erlenmeyer flask containing 500 ml. of Medium B. This seed flask is shaken at 28° C. on a 160 rpm shaker (2" throw) for 36 hours at which time the growth is satisfactory.

The growth from this seed flask is used to inoculate a 189 liter stainless steel seed tank containing 160 liters of Medium B. This tank is operated at 28° C. using an agitation rate of 150 rpm and an airflow of 3 cu. ft. per minute for 24 hours. Defoamer, Polyglycol 2000 (Dow Chemical Corp.), is used as required but not to exceed 0.1%. pH determinations are made as follows:

| Age, Hours | 0 | 12 |
|---|---|---|
| pH | 6.3 | 6.35 |

Forty-three liters of the growth in this seed tank is used to inoculate a 756 liter stainless steel fermentor containing 467 liters of Medium C, wherein Medium C has the composition:

| Medium C | |
|---|---|
| Tomato Paste | 20.0 g. |
| Primary Yeast | 10.0 g. |
| Dextrin (Amidex) | 20.0 g. |
| CoCl$_2$ . 6H$_2$O | 5.0 mg. |
| Distilled H$_2$O | 1000 ml. |
| pH: adjust to 7.2–7.4 using NaOH | |

This tank is run at 25° C. using an agitation rate of 146 rpm and an airflow of 9 cu. ft. per minute for 92 hours. Additional defoamer, Polyglycol 2000, is added as required, not to exceed 0.1%. Antibacterial assays are run on *Salmonella gallinarum* MB1287, *Vibrio percolans* ATCC 8461 and the data is as follows:

| Age Hrs. | 0 | 12 | 24 | 36 | 48 | 60 | 72 | 84 | 92 |
|---|---|---|---|---|---|---|---|---|---|
| pH | 6.6 | 6.7 | 6.65 | 6.3 | 6.0 | 6.4 | 6.15 | 6.5 | 6.5 |
| MB-1287 mm. | — | — | — | S | — | 19 | 26 | 28 | 32 |
| ATCC 8461 mm. (1–10) | — | — | | S | — | 21 | 24 | 26 | 30 |
| 890A units/ml. | | | | NA | NA | 6.8 | 13/5 | 24.9 | 24.3 |

The 890A units/ml. are determined as set forth in the section with the heading "II. Assay Procedure for Determining '890 Assay Units'."

One-hundred-twenty-five gallons of broth are chilled to 5° C. and centrifuged through a Titan P-9 centrifuge. Fifty pounds of Celite is added to the 100 gallons of supernatant, and the suspension filtered through a Shriver 18-inch filter press. The 91 gallons of filtrate is adsorbed to a column containing seven gallons of Dowex-1×2 (Cl⁻), 50–100 mesh, and the column is washed with 10 gallons of deionized water, followed by thirty gallons of 5% NaCl+0.01 M Tris-HCl buffer, pH 7.0+25 μM neutral EDTA in deionized water. After an additional wash of 5 gallons of deionized water, the antibiotics 890A$_2$ and 890A$_5$ are eluted with twenty-five gallons of 3% NaCl+0.01 M Tris-HCl buffer, pH 7.0+25 μM neutral EDTA in 50% (v/v) aqueous methanol. Five gallon fractions are collected.

Antibiotic activity determined by assay against *Salmonella gallinarum* MB1287 appears in fractions 1 through 5 with a maximum at fraction 3. Fractions 2 and 3, containing 10.9% of the activity of the applied broth, are combined and concentrated to 2 gallons under reduced pressure. The concentrated sample is diluted with 8 gallons of deionized water and again concentrated to 2 gallons under reduced pressure, to eliminate residual methanol.

The two gallons of concentrate are applied to a column containing 10 gallons of XAD-2 which had been previously washed with 50 gallons of 60% aqueous acetone followed by 50 gallons of deionized water and 50 gallons of 5% NaCl. The column is eluted with 37.5 gallons of deionized water. Three fractions of 2.5 gallons followed by six fractions of five gallons are collected. The activity, as determined by assay on *Salmonella gallinarum* MB1287 plates, appears in fractions 1 through 6, with a peak of potency in fraction 2. Fractions 2 through 5, containing 64% of the activity to the XAD column or 520,000 units, are pooled.

Fractions 2 through 5 are concentrated to 120 ml. by evaporation under reduced pressure. The pH is adjusted to 6.5 and the concentrate is applied to a column (7×50 cm.) of XAD-2 which had been washed with 8 liters of 60% aqueous acetone followed by 4 liters of deionized water and 8 liters of 5% NaCl in deionized water. The sample is drained to bed level and the column is rinsed with three 20 ml. portions of deionized water, draining to bed level each time. The antibiotic is eluted with six liters of deionized water at a flow rate of 40 ml. per minute. Eight fractions of 200 ml. followed by eleven fractions of 400 ml. are collected. Antibiotic activity, as determined by assay on *Salmonella gallinarum* MB1287 plates, appears in fractions 3 through 18, with a peak of activity in fraction 8.

Fractions 8 through 12, having the highest ratios of bioactivity/A$_{220}$, and having 225,000 bioactivity units, determined by assay against *Salmonella gallinarum* MB1287, are combined for further processing.

The combined fractions are concentrated under reduced pressure to 50 ml., and 50 ml. of methanol are added. The sample is applied on a column of Dowex-1×4 (Cl⁻), minus 400 mesh, bed dimensions 2.2×40 cm., which had been previously washed with 50% methanol. The column is eluted with two liters of 0.07 M NaCl+0.005 M NH$_4$Cl+0.0001 M NH$_3$ in 50% aqueous methanol, at a flow rate of 2 ml. per minute. Fractions of 12 ml. are collected.

Two unequal peaks of bioactivity, as determined by assay against *Salmonella gallinarum* MB1287, are observed in the effluent, corresponding to two peaks of material with an absorption maximum at 308 nm. Most of the absorbance at 308 nm in both peaks is extinguishable by reaction with hydroxylamine.

The first peak, containing 890A$_2$, appears in fractions 98 through 136, and the second peak, containing 890A$_5$, appears in fractions 136 through 158. Fractions 112 through 130 are combined to give the 890A$_2$ Dowex pool, and fractions 138 through 148 are combined to give the 890A$_5$ Dowex pool. The 890A$_2$ is further purified by desalting on Sephadex G-10.

Fractions 112 through 130 containing 890A$_2$, are concentrated under reduced pressure to 5.5 ml. and the concentrate is applied to a column (2.15×70 cm.) of Sephadex G-10, and eluted with deionized water at a flow rate of 1 ml. per minute. Fractions of 2.85 ml. each are collected. The bioactivity as determined by assay against *Salmonella gallinarum* MB1287 appears in fractions 60 through 98. Fractions 78 through 90 have the highest A$_{308}$/A$_{260}$ ratios, and these are pooled for lyophilization. The pH of the pooled fractions is 4.1, and is adjusted to 7.8 by addition of 8 μl of 1 M ammonia. The pool contains 52 A$_{308}$ units with an A$_{308}$/A$_{260}$ ratio of 0.76, demonstrating substantial degradation of the antibiotic during this procedure.

The pooled fractions 78 through 90 are concentrated to 1.69 ml. under reduced pressure. Two 0.1 ml. samples are removed and lyophilized separately in small conical glass reaction vials. The remainder is lyophilized in a 14 ml. glass screw-cap vial, giving 1.29 mg. of solids, containing 890A$_2$.

EXAMPLE 4

Preparation of 890A$_5$

A tube of lyophilized culture of *Streptomyces flavogriseus* MA-4434 is opened aseptically and the contents suspended in a tube containing 0.8 ml. of sterile Davis salts having the following composition:

| Davis Salts | |
| --- | --- |
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of medium A having the following composition:

| Medium A | |
| --- | --- |
| Glycerol | 20.0 g. |
| Primary Yeast | 5.0 g. |
| Fish Meal | 15.0 g. |
| Distilled H$_2$O | 1000 ml. |
| Agar | 20.0 g. |
| pH: adjust to 7.2 using NaOH | |

The inoculated slants are incubated for one week at 27°–28° C. and then stored at 4°–6° C. until used (not longer than 21 days).

Ten ml. of medium B having the composition:

| Medium B | |
| --- | --- |
| Yeast Autolysate (+Ardamine) | 10.0 g. |
| Glucose | 10.0 g. |
| Phosphate Buffer* | 2.0 ml. |
| MgSO$_4$ . 7H$_2$O | 50 mg. |
| Distilled H$_2$O | 1000 ml. |
| pH: adjust to 6.5 using HCl or NaOH | |

[30] Ardamine: Yeast Products Corporation
*Phosphate Buffer solution
KH$_2$PO$_4$        91.0 g.

| | |
|---|---|
| -continued | |
| Na$_2$HPO$_4$ | 95.0 g. |
| Distilled H$_2$O | 1000 ml. | is transferred aseptically to one of these slants, the spores and aerial mycelia scraped into suspension, and this suspension used to inoculate three 2 liter baffled Erlenmeyer flask containing 500 ml. of Medium B to the extent of 3.3 ml./flask. These seed flasks are shaken at 28° C. on a 160 rpm shaker (2" throw) for 36 hours at which time the growth is satisfactory.

Five hundred ml. of the growth from these seed flasks is used to inoculate a 189 liter stainless steel seed tank containing 160 liters of Medium B. This tank is operated at 28° C. using an agitation rate of 150 rpm and an airflow of 3 cu. ft. per minute for 24 hours. Defoamer, Polyglycol 2000 (Dow Chemical Corp.), is used as required but not to exceed 0.1%. pH determinations are made as follows:

| Age, Hours | 0 | 24 |
|---|---|---|
| pH | 6.1 | 5.6 |

Forty-three liters of the growth in this seed tank is used to inoculate a 756 liter stainless steel fermentor containing 460 liters of Medium C, wherein Medium C has the composition:

| Medium C | |
|---|---|
| Tomato Paste | 20.0 g. |
| Primary Yeast | 10.0 g. |
| Dextrin (Amidex) | 20.0 g. |
| CoCl$_2$ . 6H$_2$O | 5.0 mg. |
| Distilled H$_2$O | 1000 ml |
| pH: adjust to 7.2–7.4 using NaOH | | which had been sterilized 60 minutes at 120° C. This tank is run at 25° C. using an agitation rate of 160 rpm and an airflow of 10 cu. ft. per minute for 144 hours. Additional defoamer, Polyglycol 2000, is added as required, not to exceed 0.1%. Antibacterial assays are run on *Salmonella gallinarum* MB1287, *Vibrio percolans* ATCC 8461 and the data is as follows:

| Age in Hours | 0 | 24 | 48 | 72 | 96 | 120 | 144 |
|---|---|---|---|---|---|---|---|
| pH | 6.2 | 6.2 | 6.2 | 7.0 | 7.3 | 7.7 | 8.2 |
| MB1287 mm | — | T | 26.5 | 28 | 33.5 | 32.5 | 31.5 |
| MB1272 mm (1–10 dil.) | — | 21.5 | 26.5 | 35 | 31.5 | 33 | |
| 890A units/ml | — | 6.4 | 16.5 | 16.7 | 22.5 | 19.5 | |

The 890A units/ml. are determined as set forth in the section with the heading "II. Assay Procedure for Determining '890 Assay Units'."

One hundred gallons of broth are chilled to 5° C. and centrifuged through a Titan P-9 centrifuge. Forty pounds of Celite are added to the 75 gallons of supernatant, and the suspension filtered through a Shriver 18-inch filter press. The 60 gallons of filtrate are adsorbed to a column containing seven gallons of Dowex-1×2 (Cl$^-$), 16–100 mesh, and the column is washed with ten gallons of deionized water followed by thirty gallons of 5% NaCl+0.01 M Tris-HCl buffer, pH 7.0+25 μM neutral EDTA. After an additional wash of 5 gallons of deionized water, the antibiotics 890A$_2$ and 890A$_5$ are eluted with thirty-five gallons of 3% NaCl+0.01 M Tris-HCl, pH 7.0+25 μM neutral EDTA in 50% methanol. Fractions of five gallons each are collected.

The bioactivity, determined by assay against *Salmonella gallinarum* MB1287, appears in fractions 1 through 7 with a maximum at fraction 3.

Fractions 3 through 7, containing 18% of the applied activity, are concentrated under reduced pressure to 2.5 gallons and the concentrate is applied to a column containing 10 gallons of XAD-2 which had been previously washed with 50 gallons each of 60% (v/v) aqueous acetone, deionized water, and 5% NaCl in deionized water. The antibiotics 890A$_2$ and 890A$_5$ are eluted with 35 gallons of 25 μM neutral EDTA in deionized water. One fraction of 5 gallons followed by four fractions of 2.5 gallons and four fractions of 5 gallons are collected. Bioactivity, determined by assay against *Salmonella gallinarum* MB1287, appears in fractions 3 through 9, with a maximum at fraction 4.

Fractions 3 through 6, containing 18% of the activity of the filtered broth, are combined and concentrated under reduced pressure to 122 ml., and the concentrate is adjusted to pH 6.45 by addition of 5 ml. of 1 M HCl. The concentrate is applied on a column (7.9×60 cm.) of XAD-2 which had been previously washed with 16 liters each of 60% aqueous acetone, deionized water, and 5% NaCl in deionized water. The antibiotics 890A$_2$ and 890A$_5$ are eluted with 8 liters of deionized water at a flow rate of 50 ml. per minute. Fractions of from 200 to 1000 ml. are collected.

Bioactivity, determined by assay against *Salmonella gallinarum* MB1287, appears in fractions 5 through 20, being from 1900 to 7700 ml. of eluted volume. The A$_{220}$, and HAEA$_{304}$ values are also measured on fractions 9 through 20. Fractions 9 through 12 have 261–286 bipotency units per HAEA$_{304}$ unit, and fractions 16 through 20 have 23–28 units/HAEA$_{304}$ unit, and fractions 13 to 16 have intermediate values, demonstrating a significant separation of antibiotics 890A$_2$ and 890A$_5$ on this column. Fractions 15 through 19, containing mostly 890A$_5$, are pooled for further purification.

The pooled fractions, 15 through 19, are concentrated under reduced pressure to 250 ml. To the concentrate are added 250 ml. of methanol, and the sample applied at a flow rate of 2 ml. per minute to a column (3.4×50 cm.) of Dowex-1×4 (Cl$^-$), minus 400 mesh, which had been washed with 50% methanol. The column is eluted with 8 liters of 0.1 M NaCl+0.005 M NH$_4$Cl+0.0001 M NH$_3$ in 50% methanol at a flow rate of 2 ml. per minute. Fractions of 10 ml. are collected.

Antibiotic 890A$_5$ elutes in fractions 505 through 605 with a peak at fraction 550. Fractions 520 through 580 are pooled, and a 300 ml. portion of the pool is removed and concentrated to 4 ml. under reduced pressure. To the concentrate is added 6 ml. of methanol and 25 μl. of 1 M NaOH, giving a final pH of 7.3.

The pH-adjusted concentrate is applied on a column (2.2×70 cm.) of Sephadex G-10 which had been equilibrated with 0.02 mM NH$_3$ in 50% methanol. The column is eluted with 0.02 mM NH$_3$ in 50% methanol at a flow rate of 1 ml. per minute.

The 890A$_5$ elutes in fractions 38 through 88 with a maximum at fractions 39 and 40. Fractions 40 through 68 are combined and the pH adjusted from 6.3 to 6.8 with 1 M NaOH. The pooled fractions, 40 through 68, are concentrated to 4 ml. under reduced pressure, and 80 μl. of 1 M NaOH are added during the concentration to maintain the pH between 7.0 and 7.3. To the final 4 ml. of concentrate, 20 μl. of 1 M NaOH are added, bringing the pH to 7.4.

The concentrate is further purified by applying on a column (3.4×46 cm.) of Dowex-50×2 (Na+), 200–400 mesh, which had been washed with 4 liters of 0.2 mM NaOH followed by 800 ml. of deionized water. The antibiotic is eluted with deionized water at a flow rate of 4.1 ml. per minute. Fractions of 8.2 ml. are collected.

The antibiotic appears in fractions 22 through 27 with a maximum at fraction 23. Fractions 23 through 25 are pooled, containing 152 $A_{308}$ units with a ratio $A_{308}/A_{260}$ of 2.00. Conductivity measurements indicate the presence of 70 μmoles of NaCl in the pooled fractions.

A 4 ml. portion of the pooled Dowex-50 fractions 23–25 is converted to the ammonium form by passage over a column (0.7 cm.×12 cm.) of Dowex-50×2 ($NH_4^+$), 200–400 mesh, which had been washed with 100 ml. of 0.1 mM $NH_3$ followed by 10 ml. of deionized water. The sample is eluted with deionized water, collecting fractions of 1 to 2 ml. All fractions with $A_{308}$ greater than 1 are combined, giving a total of 6 ml. with $A_{308} = 30$. This sample is concentrated under reduced pressure to 0.725 ml., and two 50 μl. aliquots are pipetted separately into 2 conical 0.5 ml. reaction vials and lyophilized.

Trimethyl-silylation of antibiotic $890A_5$ results in three different derivatives: a di- and a tri-methylsilyl derivative (M.W.s 456 and 528, respectively) and a small amount of a tetra-trimethylsilyl derivative of a hydrolysed product (M.W. 618) wherein the β-lactam ring is open.

The values of the most important mass spectral fragment are given below:
  di-trimethylsilyl derivative: 441; 299; 298 and 84;
  tri-trimethylsilyl derivative: 513; 371 and 156;
  tetra-trimethylsilyl derivative (only low-resolution signal observed): 618 and 603.

A 18.6 ml. portion of the pooled Dowex-50 fractions 23–25 is concentrated to 3 ml. under reduced pressure, and a 1.96 ml. aliquot is frozen and lyophilized in a 14 ml. glass vial to give 2.73 mg. of solids containing a mixture of antibiotic $890A_5$ and sodium chloride. Since the conductivities of fractions 23–25 indicated that 45% of the solids consisted of sodium chloride, an E% of 490 at 308 nm can be calculated for a salt-free sample of $890A_5$, from the observed E% of 272. The 1.0 ml. remaining from the 3.0 ml. of concentrate is lyophilized separately for NMR analysis.

The following table lists the 100 NHz-NMR signals for $890A_5$ sodium salt in $D_2O$ relative to the internal standard DSS; chemical shifts are given in ppm and coupling constants in Hz; the apparent multiplicities are indicated.

1.29 (d, J=6.2, C$\underline{H}_3$—CH); 2.05 (S, CH$_3$C=O); 3.09 (app. d of d, C—C$\underline{H}_2$—C); 3.41 (d of d, J=5.0, 3.0, >C$\underline{H}$—C=O); 4.16 (m, >CH—N and >C$\underline{H}$—OH); 6.00 and 7.11 (doublets, J=13.8, S—CH=CH—N).

EXAMPLE 5

Shake Flask Production of Antibiotic $890A_1$

A tube of lyophilized culture of *Streptomyces flavogriseus* MA-4600 is aseptically opened and the contents suspended in a tube containing 1.5 ml. of sterile medium A having the following composition:

| Medium A | |
|---|---|
| Yeast Extract | 10.0 g. |
| Glucose | 10.0 g. |
| MgSO$_4$ . 7H$_2$O | 0.05 g. |
| *Phosphate Buffer | 2 ml. |
| Distilled H$_2$O | 1000 ml. |
| *Phosphate Buffer Solution | |
| KH$_2$PO$_4$ | 91.0 g. |
| Na$_2$HPO$_4$ | 95.0 g. |
| Distilled H$_2$O | 1000 ml. |

This suspension is used to inoculate a 250 ml. triple-baffled Erlenmeyer seed flask containing 54 ml. of seed medium B having the following composition:

| Medium B | |
|---|---|
| Autolyzed Yeast (Ardamine+) | 10.0 g. |
| Glucose | 10.0 g. |
| MgSO$_4$ . 7H$_2$O | 0.05 g. |
| *Phosphate Buffer | 2 ml. |
| Distilled H$_2$O | 1000 ml. |
| pH: adjust to 6.5 with NaOH | |
| +Ardamine: Yeasts Products Corporation | |
| *Phosphate Buffer Solution | |
| KH$_2$PO$_4$ | 91.0 g. |
| Na$_2$HPO$_4$ | 95.0 g. |
| Distilled H$_2$O | 1000 ml. |

The seed flask is stoppered with cotton and shaken for 30 hours at 28° C.±1° C. on a 220 rpm gyrotory shaker (2" throw).

Fifty 250 ml. unbaffled Erlenmeyer production flasks, each containing 40 ml. of production medium C are inoculated with 1 ml. per flask of the broth from the seed flask. The production flasks are stoppered with cotton.

| Medium C | |
|---|---|
| Tomato paste | 20.0 g. |
| Primary yeast | 10.0 g. |
| Dextrin (Amidex) | 20.0 g. |
| CoCl$_2$ . 6H$_2$O | 5.0 mg. |
| Distilled H$_2$O | 1000 ml. |
| pH: adjust to 7.2–7.4 with NaOH | |

After inoculation, the production flasks are incubated at 28° C.±1° C. with shaking on a 220 rpm gyrotory shaker (2" throw) for 3 days. The flasks are assayed for activity against standard *Vibrio percolans* ATCC 8461 assay plates using ½ inch assay discs dipped into centrifuged fermentation broth samples. Samples are diluted with 0.05 M phosphate buffer, pH 7.4. The results are tabulated below:

| Harvest Age hours | 72 |
|---|---|
| pH | 6.4 |
| *Vibrio percolans* | |
| (1/100 Dilution) Assay | 23 mm. |
| 890 Assay, units/ml. | 103 |

The 890A units/ml. are determined as set forth in the section with the heading "II. Assay Procedure for Determining '890 Assay Units'".

The whole broth is centrifuged in 200 ml. portions in polycarbonate bottles at 9000 rpm for 15 minutes to give 1600 ml. of combined supernatants with a potency of 104 units/ml. To this is added 0.5 ml. of 0.1 M neutral EDTA.

The centrifuged broth is adsorbed on a Dowex-1×2 (Cl⁻), 50–100 mesh column, bed dimensions 3.8×22 cm., at a flow rate of 6 to 20 ml./min. The column is rinsed with 100 ml. of deionized water and eluted with 1 liter of deionized water containing 50 g. of sodium chloride, 0.02 M Tris HCl buffer, pH 7.0, and 25 $\mu$M neutral EDTA, at a flow rate of 6 ml./min. Fractions of 10 ml. are collected.

Antibiotic $890A_1$ appears in fractions 13 through 81, with a maximum at fractions 25 to 33, counting from the first application of salt eluate. Fractions 24 through 41, having the highest biopotency/$A_{220}$ ratios, are combined for further processing. The combined fractions have a total of 29,000 units, or 17% of the applied bioactivity.

The Dowex eluate is concentrated to 10 ml., the pH is adjusted to 6.5 with dilute hydrochloric acid, and the concentrate is applied on a column of XAD-2, bed dimensions 3.3×36 cm., which had been previously washed with 2 liters each of 60% aqueous acetone, deionized water, and 5% (w/v) sodium chloride in deionized water. The sample is eluted with deionized water at a flow rate of 6 ml./min. Fractions of 40 to 260 ml. are collected.

Antibiotic activity appears in fractions 6 through 14, extending from 220 to 2560 ml. of eluted volume. The peak is at fractions 9 and 10, extending from 370 to 590 ml. of eluted volume. Fractions 9 through 12, extending from 370 to 1060 ml. of eluted volume, have the highest ratios of $HAEA_{300}/A_{220}$, and are combined for further processing. These fractions have 36,600 units, equal to 126% of the apparent applied activity.

The combined fractions 9 through 12 are concentrated to 100 ml. and the concentrate applied on a column of Dowex-1×4 (Cl⁻), minus 400 mesh, bed dimensions 2.2×41 cm., at a flow rate of 2 ml./min. The column is rinsed with 50 ml. of deionized water, and eluted with 3 liters of 0.07 M NaCl+0.005 M NH₄Cl+0.0001 M NH₃ in deionized water, at a rate of 2 ml./min. Fractions of 10.8 ml. are collected, starting from the first application of eluent.

The main peak of antibiotic $890A_1$ appears in fractions 181 through 217, with a maximum at fraction 198. Fractions 186 through 210, containing a total of 114 absorption units at 300 nm., are pooled.

The pooled fractions are concentrated to 4.0 ml., and the pH is adjusted to 7.3 by addition of 16$\mu$ liter of 1 M NaOH. The concentrate is applied on a column of Bio-Gel P-2, 200–400 mesh, bed dimension 2.15×70 cm., and is washed in with 3×1 ml. washes of deionized water and eluted with deionized water at 0.96 ml./min. Fractions of 3.85 ml. are collected.

The main peak of antibiotic $890A_1$ appears in fractions 24 through 44, with a maximum at fractions 33 and 34. Fractions 27 through 38, having the highest $A_{300}/A_{245}$ ratios, are combined for lyophilization. These combined fractions have a total of 72 $A_{300}$ units.

To carry out the lyophilization, the combined fractions are concentrated to 3.0 ml. and the pH of the concentrate is adjusted to 7.5 by addition of 10$\mu$ liters of 0.1 M NaOH. The sample is divided into two portions of 1.50 ml. each, and the portions are separately quick-frozen and lyophilized from 14 ml. glass screw-cap vials. Each sample contains 1.73 mg. of $890A_1$, corresponding to 35.8 $A_{300}$ units.

FORMULATION CONTAINING ANTIBIOTICS $890A_2$ and $890A_5$

Compositions containing the antibiotics of the present invention may be administered in several unit dosage forms as, for example, in solid or liquid orally ingestible dosage form. It will be apparent that the antibiotics $890A_2$ and $890A_5$ can be used separately or in combination. The compositions described below apply to antibiotics $890A_2$ and $890A_5$ alone and in combination. The quantities of antibiotic $890A_5$ administered will, in general, be larger than the quantities of $890A_2$ for any given clinical situation. The compositions per unit dosage, whether liquid or solid may contain from 0.1% to 99% of active material, the preferred range being from about 10 to 60%. The composition will generally contain from about 100 mg. to about 2000 mg. by weight of the active ingredient based upon the total weight of the composition; however, in general, it is preferable to employ a dosage amount in the range of from about 250 mg. to 2000 mg. In parenteral administration the unit dosage is usually the pure compound in a sterile water solution or in the form of a soluble powder intended for solution. Representative formulations can be prepared by the following procedures:

| Capsules | Per Capsule |
|---|---|
| Antibiotic $890A_2$ | 400 mg. |
| Lactose U.S.P., a sufficient quantity to fill No. 0 Capsules, approx. 475 mg. each | |

In the above example the active compound and the diluent are mixed to produce a uniform blend, which is then filled into No. 0 hard gelatin capsules, by hand or on a suitable machine, as required. The mixing and filling is preferably done in an area having a relative humidity less than 40%.

| Tablets | Per Tablet |
|---|---|
| Antibiotic $890A_2$ | 330. mg. |
| Calcium phosphate | 192. mg. |
| Lactose, U.S.P. | 190. mg. |
| Cornstarch | 80. mg. |
| Magnesium stearate | 8. mg. |
| | 800. mg. |

In the above example, the active component is blended with the calcium phosphate, lactose and about half of the cornstarch. The mixture is granulated with a 15% cornstarch paste and rough-screened and screened again through No. 16 screens. The balance of the cornstarch and the magnesium stearate is added and the mixture is compressed into tablets, approximately ½" in diameter, each weighing 800 mg.

Alternatively, the active component is blended with the calcium phosphate, lactose and one-half the cornstarch. The mixture is "slugged" on a heavy duty press to produce compacted tablet-like masses. These are broken down to a No. 16 mesh granule. The balance of the cornstarch and the magnesium stearate are added and the mixture is compressed into tablets approximately ½" in. diameter, each weighing 800 mg.

| Lyo Form (For Injection) | Per Vial |
|---|---|
| Antibiotic $890A_2$ | 500 mg. |

| Lyo Form (For Injection) | Per Vial |
|---|---|
| Water-for-Injection, U.S.P. to make | 2 ml. |

In the above example the active component is dissolved in sufficient water-for-injection in the ratio shown. The solution is filtered through Selas candles or Millipore membrane filters to sterilize. The solution is subdivided into sterile vials. The vials and contents are frozen, and the water is aseptically removed by lyophilization. The vials containing the sterile dry solid are aseptically sealed.

To restore for parenteral administration, 2 ml. of sterile water-for-injection is added to the contents of a vial.

| Oral Liquid Forms | Per 1000 ml. |
|---|---|
| Antibiotic 890A$_2$ | 1.0 gm. |
| Sucrose | 600.0 gm. |
| Glucose | 250.0 gm. |
| Sodium Benzoate | 1.0 gm. |
| Concentrated Orange Oil | 0.2 ml. |
| Purified water U.S.P. to make | 1000.0 ml. |

The sucrose and glucose are dissolved in about 400 ml. of water using heat to aid solution. This solution is cooled and sodium benzoate, followed by the concentrated orange oil added. The solution is brought to about 900 ml. volume with water and the antibiotic is added. The solution is clarified by filtration through a coarse filter.

What is claimed is:

1. A process for the production of the compound 890A$_2$ which comprises cultivating the microorganism *Streptomyces flavogriseus* NRRL 8139 or NRRL 8140 in an aqueous nutrient medium containing assimilable sources of carbon, nitrogen and inorganic salts under submerged aerobic conditions to provide a mixture comprising compound 890A$_2$ and compound 890A$_5$ and recovering compound 890A$_2$.

2. A process for the product of the compound 890A$_5$ which comprises cultivating the microorganism *Streptomyces flavogriseus* NRRL 8139 or NRRL 8140 in an aqueous nutrient medium containing assimilable sources of carbon, nitrogen and inorganic salts under submerged aerobic conditions to provide a mixture comprising compound 890A$_2$ and compound 890A$_5$ and recovering compound 890A$_5$.

* * * * *